United States Patent [19]

Kielbasiewicz

[11] Patent Number: 5,529,073
[45] Date of Patent: Jun. 25, 1996

[54] METHOD AND APPARATUS FOR RECORDING PHYSIOLOGIC SIGNALS

[75] Inventor: Peter Kielbasiewicz, Ostelsheim, Germany

[73] Assignee: Hewlett-Packard Company, Palo Alto, Calif.

[21] Appl. No.: 149,121

[22] Filed: Oct. 22, 1993

Related U.S. Application Data

[63] Continuation of Ser. No. 53,954, Apr. 26, 1993, abandoned, which is a continuation of Ser. No. 886,967, May 21, 1992, abandoned.

[51] Int. Cl.⁶ .................................................. G06F 159/00
[52] U.S. Cl. .................... 128/696; 128/698; 128/712; 128/715; 128/660.04
[58] Field of Search ............... 364/413.01, 413.02, 364/480, 486, 487, 487; 128/660.04, 661.07, 661.08, 696, 698, 700, 710, 712, 715; 324/121

[56] References Cited

U.S. PATENT DOCUMENTS

| | | | |
|---|---|---|---|
| 2,221,115 | 11/1940 | Shepard, Jr. | 324/121 R |
| 3,345,625 | 10/1967 | Russel et al. | 324/121 R |
| 4,051,522 | 9/1977 | Healy et al. | 358/86 |
| 4,264,958 | 4/1981 | Rowell, Jr. et al. | 364/485 |
| 4,513,295 | 4/1985 | Jones et al. | 128/630 |
| 4,898,179 | 2/1990 | Sirota | 128/670 |
| 5,042,499 | 8/1991 | Frank et al. | 128/698 |
| 5,088,497 | 2/1992 | Ikeda | 128/600.01 |
| 5,123,420 | 6/1992 | Paret | 128/68 |
| 5,184,062 | 2/1993 | Ladwig | 324/74 |
| 5,222,028 | 6/1993 | LaBarre et al. | 364/487 |

OTHER PUBLICATIONS

HP fetal monitor demonstration, 1991 ACOG Conference.
Corometrics Medical Systems, Inc., Model 150 Fetal Monitor (1992).

*Primary Examiner*—Gail O. Hayes
*Assistant Examiner*—Frantzy Poinvil

[57] ABSTRACT

A medical monitor, such as a fetal monitor, records physiologic signals representing the same physiologic parameter, but originating from different beings, such as the heart rate traces originating from two fetuses, in particular twins. In case the two signals show a significant amount of overlap which impairs their interpretation, one of the signals is recorded with an appropriate offset. Switching between the offset mode and the non-offset mode may be performed manually or on an automatic basis.

36 Claims, 9 Drawing Sheets

METHOD AND APPARATUS FOR RECORDING PHYSIOLOGIC SIGNALS

This is a continuation of application Ser. No. 08/053,954, filed Apr. 26, 1993 which in turn is a continuation of Ser. No. 07/886,967, filed May 21, 1992 now abandoned.

FIELD OF THE INVENTION

The present invention relates to the field of medical monitoring. More specifically, it relates to fetal monitoring, wherein the fetal heart rate, as well as maternal labor, are sensed and recorded.

BACKGROUND OF THE INVENTION

Monitors for sensing and recording physiologic signals are often used to record more than a single physiologic signal. Sometimes, it happens that two physiologic signals of the same type are recorded on the same recorder or display. Such is, for example, the case if a fetal monitor is used to monitor the heart rates of two fetuses, as in the case of twins (it may also well be that two fetuses from different mothers are recorded with the same fetal monitor).

As one specific example of the problems associated with recording of multiple physiologic signals of the same type, the case of a fetal monitor will be discussed in more detail herein. However, the present invention is not limited to such monitors.

A fetal monitor picks up and records two parameters of particular importance for the assessment of fetal well-being, namely the fetal beat-to-beat heart rate and maternal labor. Various techniques are available for recording these parameters.

The best indication of the fetal heart rate may be obtained by a so-called fetal scalp electrode which is screwed into the fetal epidermis. The electrocardiogram obtained from this electrode is used to determine the fetal beat-to-beat heart rate as the inverse of the time interval between two subsequent beats.

Unfortunately, this kind of measurement (also called "direct ECG") may only be used after rupture of the membranes. Prior to that point in time, indirect methods have to be used. The most common one is the ultrasound technique, wherein ultrasound waves are transmitted in the direction of the fetal heart. The reflected ultrasound wave is subject to Doppler shift caused by the moving parts of the fetal heart, e.g., the heart walls or heart valves. The Doppler shift can be extracted from the received ultrasound wave by means of appropriate demodulation, and the inverse of the time interval between subsequent peaks in the Doppler signal reveals the beat-to-beat heart rate. Autocorrelation is a method which is particularly useful to detect the peaks in the Doppler signal.

Likewise, there are external and internal methods for recording maternal labor. The external transducers are applied to the maternal abdomen and contain usually tension-sensitive resistance elements; the intravaginal transducer is a simple pressure transducer.

Fetal monitors of this kind are typically stand-alone units, i.e., they contain the transducer electronics, the necessary hardware for processing the received signals, a display and a recorder. The recorder—such as a thermal printer—prints on a paper strip which contains two preprinted scalings, one for the fetal heart rate, and the other for maternal labor.

Some fetal monitors have meanwhile also the capability to record twins, i.e., to record the heart rate of two fetuses, by means of appropriate transducers. However, recording these two heart rates produces a problem of considerable clinical importance.

Due to the limited space available for the recorder, standard paper is used for twin monitoring. Thus, the two heart rate traces have to be printed on the same preprinted grid or scale. If the obstetrician is monitoring twins with similar or approximately equal heart rates, the two traces will therefore overlap, such that they cannot easily be distinguished, and partially cover each other. This is a serious disadvantage in clinical practice, as the beat-to-beat heart rate traces contain relatively fast spectral components (in the range of 0.5 Hz to 0.01 Hz). These spectral components—usually referred to as "variability"—contain valuable diagnostic information which may be lost when two heart rate traces overlap.

It is therefore a strong desire to increase the readability of two (or more) fetal heart rate traces in case they are recorded on the same grid of a printer (or another kind of display).

In this context, it has to be noted that only one of one hundred births concerns twins. Therefore, the provision of another printer—for example, with broader paper for an additional grid—is no acceptable solution. In contrast, it is the regular goal of the design of fetal monitors not to create a significant overhead for the rare cases of twin births.

There have already been multiple attempts in the prior art to overcome the underlying problem. One could, for example, record the two heart rate traces with lines of different thickness, or different patterns. Although this solution is undoubtedly advantageous, the variability may still be covered by the overlapping traces; for example, the thicker trace does not allow to detect reliably the components of higher frequency in the other trace.

As an alternative, one could also provide a printer with the capability to print colored traces. However, this solution suffers from two other disadvantages. The first is that a colored printer will considerably increase manufacturing expenses, and thus the cost of the monitor, and that it is more difficult to operate (for example, the colored tapes have to be exchanged from time to time). It is thus obviously not justified to spend a colored printer simply for one percent of twin births.

The other disadvantage results from clinical practice. The obstetrician, as well as the midwife are acquainted with the usual appearance of trace records and will resist to use a different technology. It has also to be taken into consideration that a different appearance of the heart rate traces may cause errors in their interpretation, such that dangerous situations of the fetus may be lost.

By the way, the latter considerations also apply to several further prior art solutions which will be discussed below. Clinical personnel is acquainted with the present appearance of fetal heart rate records, and any change of this appearance will hardly be accepted, and may give rise to diagnostic errors. Thus, it is an important demand for all fetal monitors, even in the case of twin monitoring, to provide a record which is basically similar to the records with which clinical personnel is acquainted.

Still another solution of the underlying problem is to provide recorder paper with an additional heart rate scale or grid. For reasons already discussed above, such paper cannot be broader than the paper used for a single fetus, as no extra recorder can be provided for the case of twin monitoring. Thus, the two heart rate scales provide a smaller scale factor than usual.

This latter solution is unacceptable in clinical practice. First, and as already discussed above, the outer appearance (namely the scale factor, as well as the geometric arrangement of the heart rate traces) is different from usual recordings, which may cause errors in diagnostic interpretation. For example, the midwife is acquainted with a certain geometry of a deceleration in the fetal heart rate trace. If such a deceleration is printed with a different scale factor, the decrease of the heart rate may not appear as strong as in a usual record, such that a fetal stress situation may not be detected. It has further to be taken into account that a reduced scale factor also reduces the resolution, such that heart rate variability is more difficult to detect.

One further problem associated with double scales is that different paper has to be used for the case of twin monitoring, as compared to the monitoring of a single fetus. It would obviously not be appropriate to record a single fetus on a paper with two heart rate grids, as one of the grids would not be used in this case. Therefore, the recorder paper had to be changed from time to time, which makes handling more difficult.

For the above reasons, the provision of a paper with two different heart rate grids is also not acceptable.

One has tried to avoid these drawbacks by the provision of recorder paper wherein two different scalings are printed in the same grid (an example will be discussed in the detailed description). However, this solution has also not been accepted in clinical practice. One reason therefore is that at least one of the fetal heart rate traces is printed with a different scale factor, which implies the drawbacks already discussed above. Another reason is that it is quite difficult to assign the two traces to the correct scaling. This problem has also legal aspects, as an incorrect assignment may give rise to liability questions.

One could also use the usual paper with a single heart rate grid for the case of twin monitoring and print a second, different scale with the built-in recorder. This solution would avoid the need to change the recorder paper. However, it would not solve the problem of heart rates printed in different scale factors than usual. Further, the second scale would be printed in the same color as the heart rate traces themselves, such that the traces, and the second grid, cannot easily be distinguished (usually, the grid is preprinted on the recorder paper in a color different from the heart rate traces; for example, the grid may be preprinted in green or red, and the recorder may record the heart rate traces in black).

Another disadvantage associated with the latter solution is that the recorder is considerably stressed if it has to print a second grid, such that its lifetime is reduced. If the recorder is a thermal printer, printing of vertical grid lines may also cause the paper to stick against the printing head. This effect, in turn, produces noise which is undesirable in the delivery room.

The latter disadvantages may also apply if not only one grid, but both grids are printed by the built-in recorder. Although the provision of white paper would offer the opportunity to print different grids in the case of a single fetus, as compared to twins, the recorder would be overstressed, and the problem of a different scale factor would likewise not be solved.

The above considerations show that there have been a multiplicity of attempts to solve the problems associated with twin monitoring, but that none of them provided an acceptable solution. Thus, there is a continuing need for an improved method for recording fetal heart rates originating from different fetuses.

SUMMARY OF THE INVENTION

It is therefore a major object of the present invention to provide a method for recording at least two physiologic signals using a medical monitor, wherein the physiologic signals represent the same physiologic parameter, but originate from different sources. Although the invention will now be discussed with reference to its implementation in a fetal monitor, it will be appreciated that it can be applied to other medical monitors as well, if these produce recordings of two physiologic signals of the same type in the same grid.

According to the invention, the underlying object is solved by the steps of sensing at least two physiologic signals, recording the physiologic signals on a medium having a grid with predefined scaling or grid, wherein at least one of the signals is recorded relative to the predefined scaling on the grid, and at least one of the signals is recorded with an offset relative to the predefined scaling or grid.

One basic finding of the invention is the recognition that all of the prior art approaches have primarily failed because the two fetal heart rate traces were recorded with different scale factors (or, in more technical language, different gain factors). Thus, the optical appearance of identical acceleration or deceleration patterns was different. This, in turn, was the major reason for confusion of clinical personnel, and gave rise for faulty diagnostic interpretation.

One basic approach of the present invention is therefore to record the two traces with basically the same scale factor. Separation of the two heart rates is, instead, performed by an offset, i.e., a shift of one of the heart rate traces.

The offset ensures that the two traces do not (or only very seldom) overlap, such that the respective patterns can be easily identified and interpreted. At the same time, the outer appearance of patterns (e.g., accelerations, decelerations and the variability) is not basically changed, such that no diagnostic errors may occur. Basically, every pattern appears in the way clinical personnel is acquainted with; the patterns may only be shifted, but are of the usual shape.

Another considerable advantage of the present invention is that no changes in the recorder, nor in the paper used, have to be made. The heart rate traces may be printed by the recorder which is anyway available, without any modification. Further, the same paper as used for single fetus monitoring may also be used for twin monitoring; therefore, no paper change is necessary, nor is there a need to keep different recorder papers on stock. Thus, the invention has also manufacturing and cost advantages.

In a preferred embodiment of the invention, additional identification means are printed as soon as one heart rate trace is recorded with an offset. These identifiers warn the user and document the offset shift. For example, the two traces may be recorded with different trace patterns, or in different colors. A preferred solution is to print at least one label assigned with the trace which is shifted and/or to repeat printing of this label in predefined distances.

Another important aspect is the selection (activation or deactivation) of the offset. It will be appreciated that an offset is not always adequate, for example if the base lines of the two heart rate traces are spaced by a sufficient amount.

In one advantageous embodiment of the invention, useractuatable switching means are provided for switching between a first mode wherein both heart rate traces are recorded in the predefined scaling, and a second mode wherein at least one of the traces is offset shifted. The user may thus easily switch (e.g. via keys or a bar code reader) between the two modes. As soon as the second mode is activated, a label (and, preferably, a vertical line) is printed which indicates offset activation. Further labels are then printed in predefined distances and preferably connected, via vertical lines, with the shifted trace. Likewise, offset deactivation may be documented in a similar manner. Examples of the trace patterns may further be printed, in order to make trace identification easier.

The necessity to activate the offset feature may also be detected on an automatic basis. For example, the number of zero crossings of the two traces over a certain time interval may be registered, wherein a need for offset activation is indicated as soon as this number exceeds a predefined or adaptable limit. A related technology is described in co-pending U.S. patent application, Ser. No. 676,853, filed Mar. 25, 1991 (Guenther Paret), which is hereby fully incorporated by reference. However, it will be appreciated that different limits will be used, depending on the question whether the necessity of an offset shift is to be detected (as in the present invention), or whether the goal is to detect coincidence (as in the co-pending application).

Another criterion for detecting the need to shift one heart rate trace is to compare the ranges of the two heart rate traces, as will be discussed in more detail below. Both criteria may be used alternatively, or in addition.

As soon as the fetal monitor detects the need to shift one heart rate trace, it may send a warning to the user (e.g., by flashing an indicator, printing a message or causing an acoustic alarm) indicating that an offset shift may be appropriate. The user may then actuate appropriate switching means. This is the "semi-automatic" mode of operation. An alternative solution is the fully-automatic mode, wherein the monitor automatically switches the offset shift ON or OFF, depending on the actual trace patterns. In the latter case, a hysteresis is preferably provided, in order to ensure that switching is not effected too often.

The present invention also relates to a corresponding apparatus. More features and advantages of the present invention may be found in the claims and the detailed description.

BRIEF DESCRIPTION OF THE DRAWINGS

The invention will now be explained, by means of a non-limiting example, with reference to the accompanying drawings, in which.

DETAILED DESCRIPTION OF THE DRAWINGS

Figure 1:
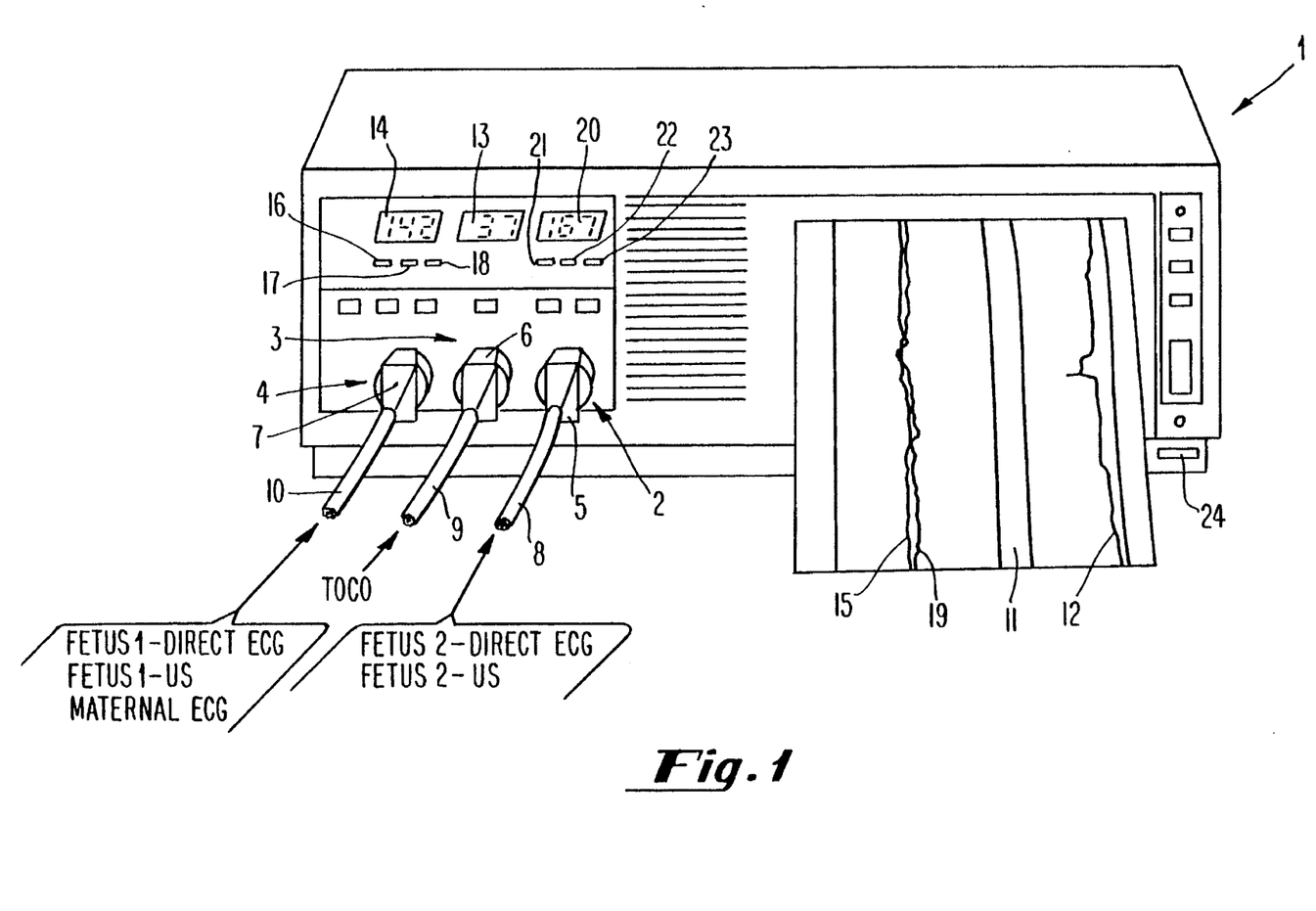
FIG. 1 depicts a perspective view of a fetal monitor able to record the heart rate of twins.

FIG. 1 depicts a fetal monitor or cardiotocograph. The fetal monitor is used to monitor the heart rate of a fetus (unborn baby) during pregnancy and labor. At the same time, the fetal monitor records uterus (or labor) activity. Simultaneous assessment of the fetal heart rate (FHR) and uterus activity (toco) allows a precise determination of the fetal condition.

Fetal monitor 1 comprises three jacks 2, 3 and 4 for the insertion of appropriate connectors 5, 6 and 7. These connectors are linked—via cables 8, 9 and 10—with the corresponding transducers (not shown here).

As indicated by the labels in FIG. 1, jack 3 is an inlet for the toco (uterus activity) transducer. Although this is an important parameter for the assessment of the fetal condition, it is not subject of the present invention and will therefore not be discussed in detail here. The signal measured via the toco channel is recorded on a thermal printer which is built in the monitor. FIG. 1 depicts paper 11, on which the thermal printer records the parameter traces. The toco recording is denoted as 12. Further, the measured toco value is optically indicated by means of display 13, here as a combination of 7-segment displays. Jack 4 is an inlet for the fetal heart activity signal. Two different connectors 7 may be used: after rupture of the membranes, i.e. during second-stage labor and birth, a fetal scalp electrode can be used which is applied intravaginally. Although this method—also called "direct ECG (electrocardiogram)"—yields excellent results, it cannot be used in pre-birth applications and during pregnancy. In these cases, another transducer has to be used, namely an ultrasound (US) transducer (cf. the corresponding labels in FIG. 1). The ultrasound transducer emits bursts of high-frequency ultrasound waves. It further receives the ultrasound signals reflected by the maternal or fetal tissue, bones etc. In case the ultrasound bursts are reflected by moving parts of the human body, such as the valves or the walls of the fetal heart, the frequency of the reflected ultrasound waves is shifted with respect to their original frequency due to the Doppler effect. A demodulator with subsequent filters is used to obtain the Doppler signal, i.e. the signal with the Doppler frequency. Peaks in the Doppler signal are indicative of a fetal heart beat. However, as the Doppler signal is usually a quite noisy and/or disturbed signal, additional measures have to be taken to facilitate detection of the peak. The fetal monitor depicted in FIG. 1 uses an autocorrelation mechanism therefor.

In either case—i.e. regardless whether the fetal heart beat is obtained by means of a scalp electrode or an ultrasound transducer, the fetal heart rate is calculated as the inverse of the time interval between subsequent beats, the so-called beat-to-beat heart rate. This is an important feature of fetal monitors as the beat-to-beat heart rate provides valuable diagnostic information.

The detected fetal heart rate is displayed by means of a 7-segment-display 14. Further, it is recorded on the thermal printer, see fetal heart rate trace 15. Three indicators—in the embodiment of FIG. 1 backlighting modules 16, 17 and 18—indicate the quality of the signal used for fetal heart rate detection. Module 16 is a red module, module 17 a yellow module and module 18 a green module. As long as the received signal is of good quality, green module 18 is ON. When the signal is of worse quality, i.e. heart beat detection becomes questionable, yellow module 17 is switched ON, and green module 18 is switched OFF. Likewise, in case of a disturbed signal where no fetal beat-to-beat heart rate trace can be recorded, red LED 16 indicates bad signal quality.

Jack 7 further may provide a maternal electrocardiogram signal e.g. obtained by electrocardiogram electrodes, a plethysmographic transducer or the like. If this signal is provided, the maternal heart rate trace is also recorded.

Fetal monitor 1 further provides a third jack 2 for insertion of a corresponding connector 5. The latter is connected—via cable 8—with a second fetal transducer, namely a fetal scalp electrode or a second ultrasound Doppler transducer. These transducers are used in case of twins to obtain a fetal beat-to-beat heart rate trace of the second fetus as well. In case a second fetal transducer is connected, the beat-to-beat heart rate is recorded as trace 19. Further, a display 20 indicates the actual value of the second fetal heart rate trace, and backlighting modules 21, 22 and 23 (red, yellow, green) indicate the quality of the second fetal signal.

Other components of the fetal monitor such as power-on button 24 are prior art and will not be discussed here.

Figure 2:
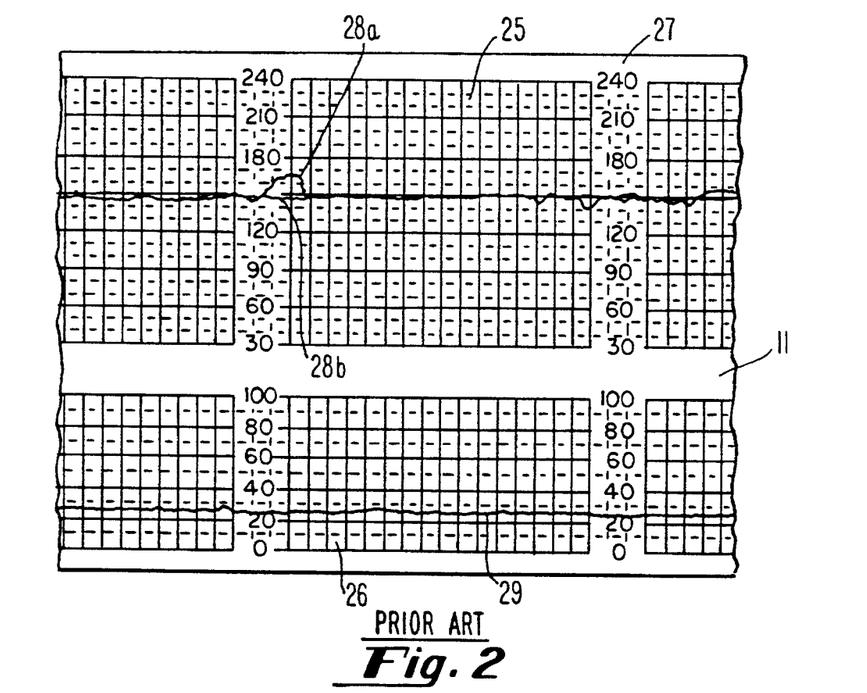
FIG. 2 shows a recorder paper with fetal heart rate and maternal labor recordings, in order to illustrate the problem underlying the present invention.

The recorder paper 11 is shown in more detail in FIG. 2. It consists of an upper grid or scaling 25 which is used to record the fetal heart rate, and a lower grid or scaling 26 for recording maternal labor (toco). Both grids or scalings also include appropriate numerics, for example numerics 27 (which labels the horizontal line which is assigned to 240 beats per minute/bpm).

The example of FIG. 2 shows the case of twin monitoring wherein two fetal heart rate traces 28a and 28b are recorded simultaneously in the same grid, and with the same scaling. It can easily be seen that the heart rate traces overlap considerably, such that the traces cannot easily be identified. Further, the components of higher frequency (variability) of a trace may be covered by the other one, such that valuable diagnostic information is lost.

The labor trace is identified as 29 in FIG. 2.

Figure 3:
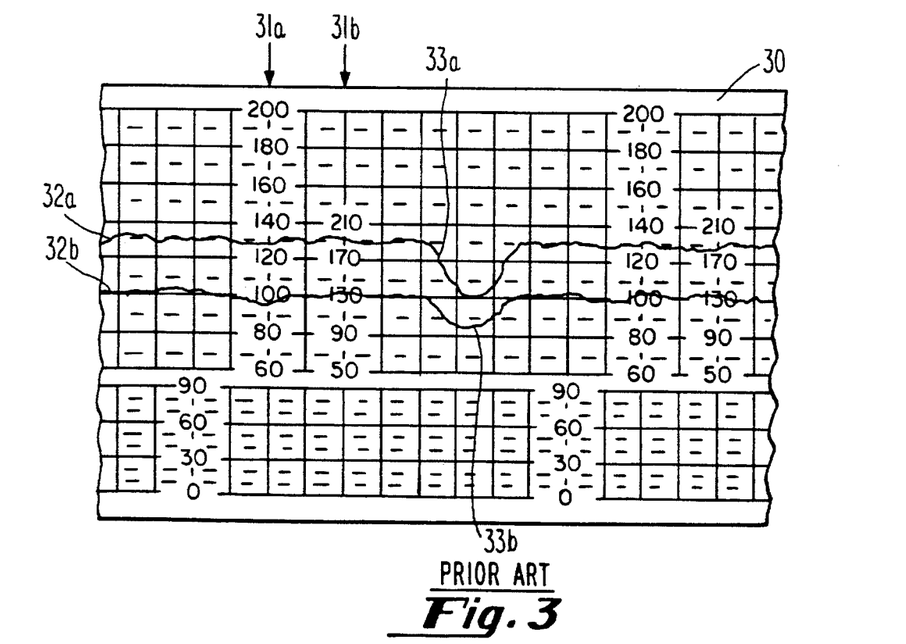
FIG. 3 depicts a recorder paper used in a prior art solution.

FIG. 3 depicts an attempt, according to the prior art, to overcome the disadvantages of simultaneous twin recording. Recorder paper 30 provides two different scalings 31a and 31b. One of heart rate traces 32a and 32b is recorded in accordance with scaling 31a, and the other one is recorded in accordance with scaling 31b. Although both heart rate traces are centered around a heart rate frequency of 130 beats per minute, the respective traces do not overlap.

However, it is evident that the assignment of either trace to the corresponding scaling is not clear. For example, it could well be that two fetuses were recorded which do not produce heart rate traces centered at 130 bpm, but that rather one fetus has a center frequency of 100 bpm, and the other one a center frequency of 190 bpm.

Still the more serious problem is that the different scale factor "deforms" events in the traces. Consider, for example, decelerations 33a and 33b. Although both patterns are intentionally identical, the different scaling factor of trace 32b changes the optical appearance of deceleration 33b. This is an important reason for diagnostic misinterpretation.

Figures 4, 5, 6:
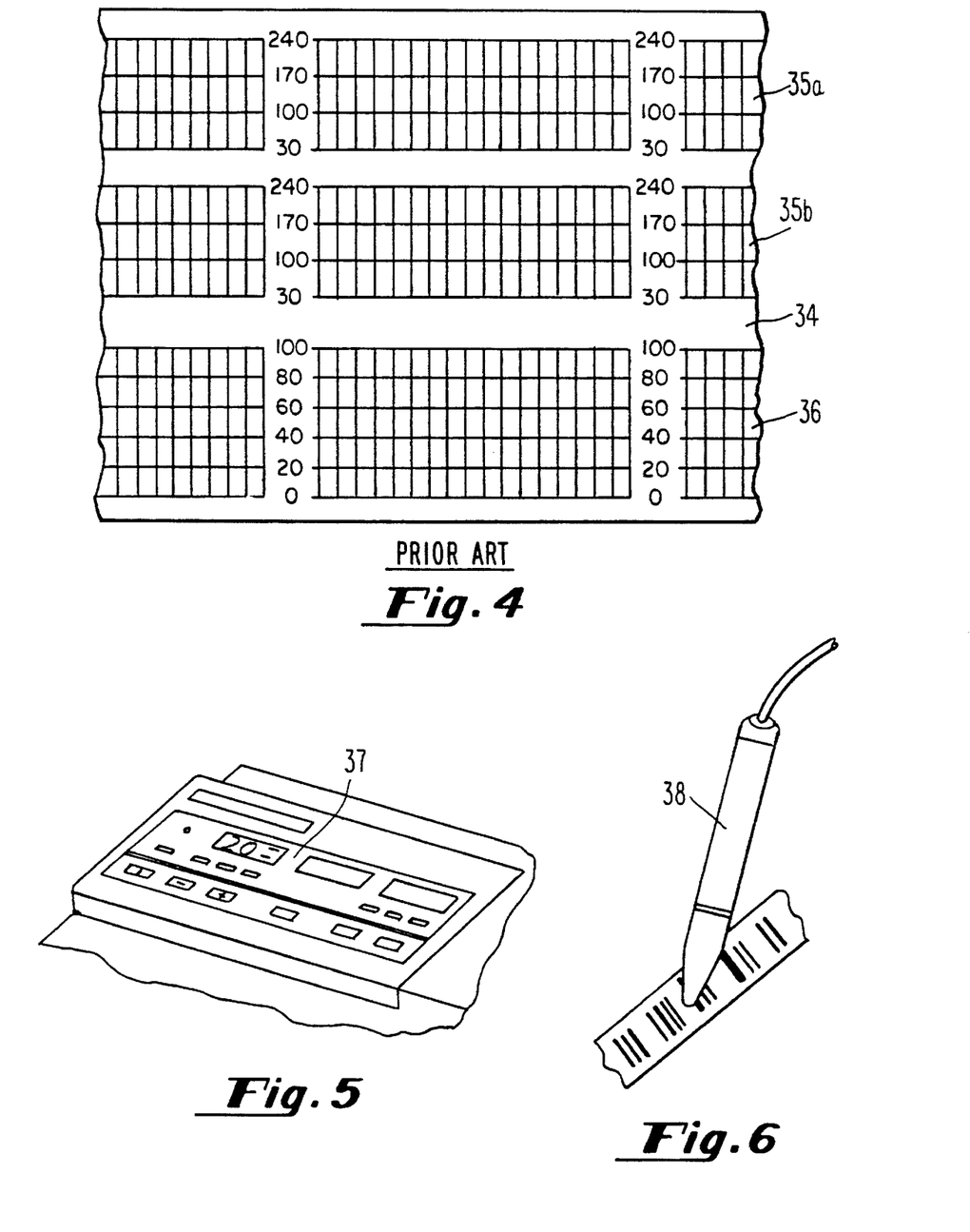
FIG. 4 shows the recorder paper according to another prior art solution.
FIGS. 5 and 6 depict means for activating the offset feature.

Yet another prior art solution is shown in FIG. 4. Recorder paper 34 includes two heart rate grids or scalings 35a and 35b (apart from the toco grid 36). The two heart rate grids 35a and 35b are provided for two respective fetuses.

It is evident that the scaling factor of grids 35a and 35b is different from a single grid (such as grid 25 in FIG. 2) which covers the same area. Thus, the solution of FIG. 4 suffers from the same disadvantage—namely deformation—as the solution of FIG. 3. Furthermore, it requires frequent paper changes, as paper 34 is not useful to record a single fetus.

The solution proposed by the present invention provides, in one embodiment, manual switching or entry means for shifting one of the heart rates. For example, a keyboard 37 (FIG. 5) can be used to activate or deactivate the offset shift, wherein such a keyboard is anyway part of commercial fetal monitors. Alternatively, a bar code reader 38, as shown in FIG. 6, may be used.

Figure 7:
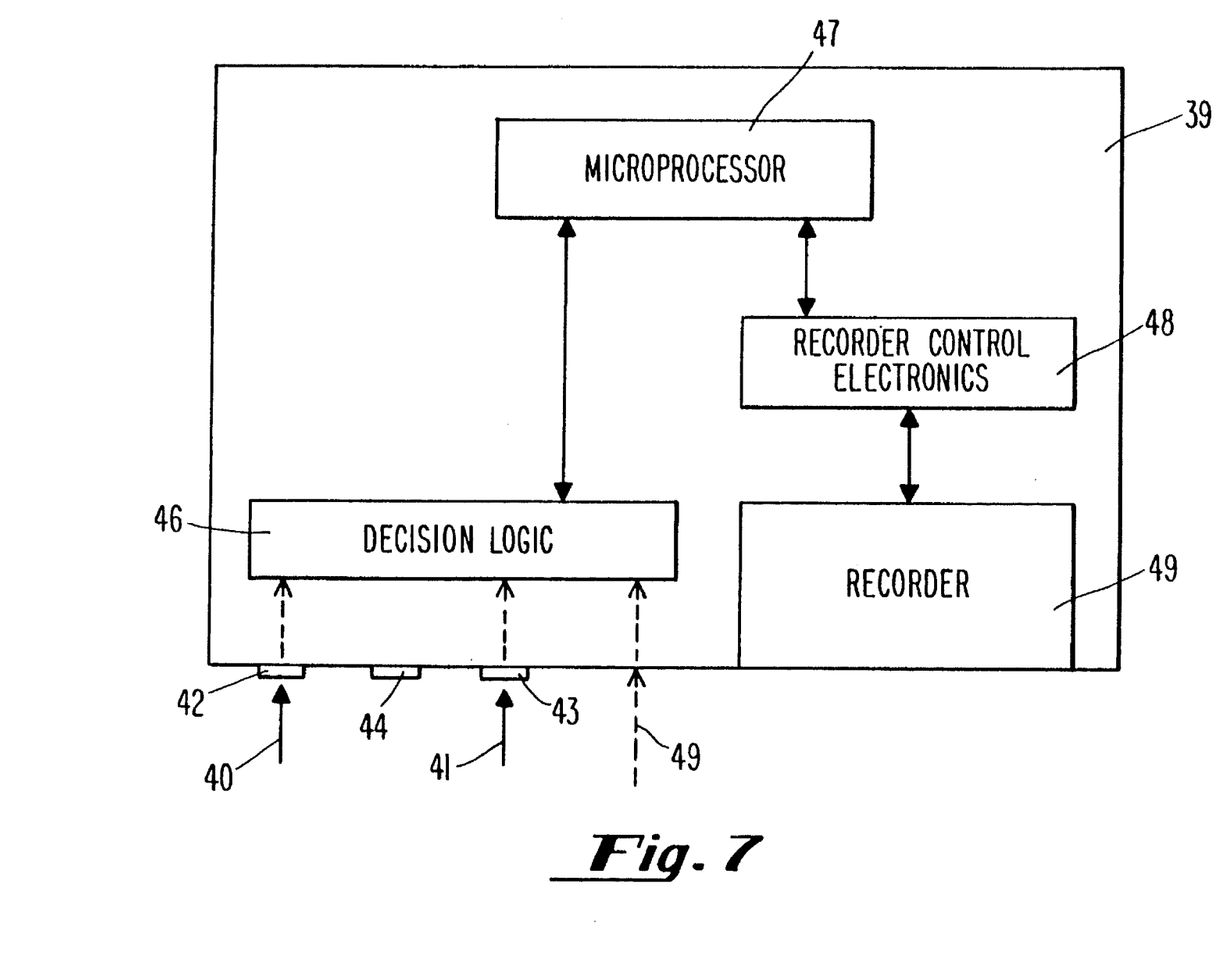
FIG. 7 depicts a block diagram of the present invention.

FIG. 7 shows a simplified block diagram of a fetal monitor 39 suited to practice the present invention. Two fetal heart rate signals 40 and 41 (which are preferably ultrasound signals, but may also be direct ECG signals or the like) are fed to appropriate jacks 42 and 43. The toco input 44 is not of further importance for the present invention.

A further, manually operated signal 45 indicates whether the offset shift should be switched ON or OFF. Manual entry means suited for this purpose have been discussed in connection with FIGS. 5 and 6. All three signals—the two heart rate signals, as well as the switching signal—are fed to a decision logic 46 under control of a microprocessor 47. The microprocessor 47 is, in turn, connected with a recorder control electronics 48 which causes recorder 49 either to print both heart rate signals with the same scaling, or to shift one of the signals.

Figure 8:
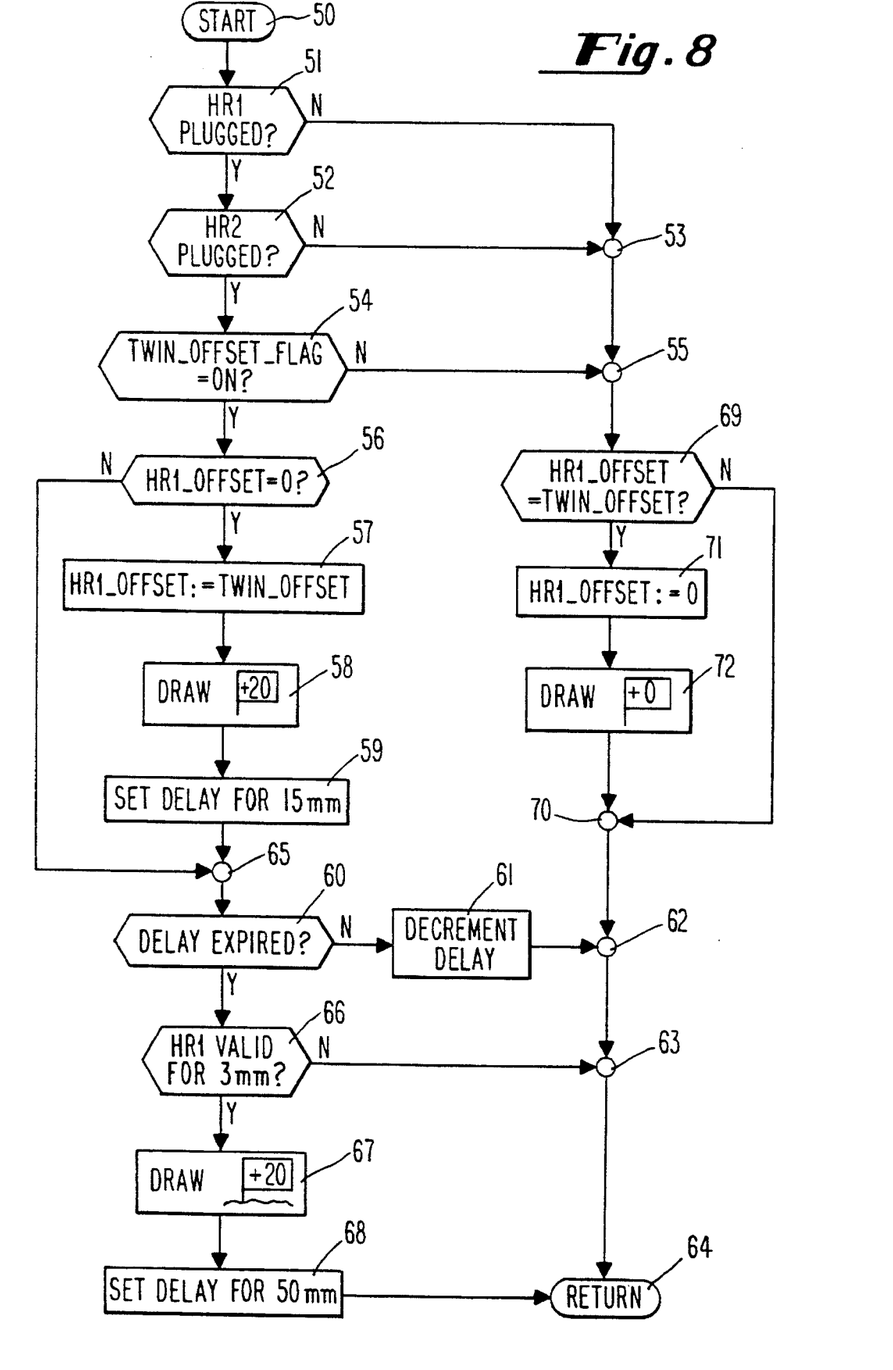
FIG. 8 is a flow chart illustrating the basic operation of a fetal monitor according to the present invention.

A basic flow chart showing the operation of decision logic 46 is shown in FIG. 8. After entry at "START" label 50, the logic first checks whether the first heart rate signal is present (step 51). It also checks whether a second heart rate signal is present, see step 52. In case either of these tests fails, only one fetus is monitored, such that any offset shift is not appropriate, and operation proceeds to node 53.

Otherwise, a variable named "Twin_Offset_Flag" is tested (step 54). This flag indicates whether the user has requested an offset shift or not. If no offset shift has been requested, operation proceeds to node 55.

However, if all test results in steps 51, 52 and 54 were positive, operation continues at step 56. In this step, the decision logic tests whether the offset feature has already been activated. If not (HR1_Offset=0), the offset of heart rate 1 is set equal to the Twin_Offset, see box 57. A start label is then printed which indicates a beginning offset. In the example shown, this is a broken vertical line and a label which includes some numerics indicating the amount of offset shift (box 58). It will be appreciated that the offset can be constant, or a user-selectable, or an adaptive value.

A delay counter is set in step 59 which indicates that the next label has to be drawn after further 15 mm of recording.

In the case discussed above, namely the start of an offset shift, the test for an expired delay in step 60 will reveal a negative result, such that operation proceeds to box 61. After decrementing the delay counter, operation continues (via nodes 62 and 63) with "RETURN" label 64.

Now let us assume that the test in step 56 revealed a negative result. This means that the offset feature has already been active. Operation thus proceeds directly to node 65. In case the delay has not yet expired, operation proceeds just as in the preceding example. Otherwise, it is tested whether the first heart rate has been valid for a trace length of at least 3 mm (step 66). If this is the case, a "flag" is drawn which includes a label showing the current offset, and which is connected with the shifted heart rate (box 67). The test in step 66 is provided in order to ensure that the flag is not connected with a very short, interrupted piece of the heart rate trace as e.g. caused by an artifact.

In step 68, the delay counter is set to repeat the "flag" after further 50 mm. It will thus be noted that the spacings between subsequent indicative markings is not always equal. Whereas the first "flag" is drawn 15 mm after the initial marking, further flags will only be drawn in distances of 50 mm.

Now, let us consider the branch after node 55. This branch is entered if the offset shift is not active. A test is performed in step 69 for the status of "HR1_Offset", in order to check whether the offset feature is already deactivated or not (similar to the test in step 56). In case the offset feature has not been active, no action is required, such that operation may continue at node 70. Otherwise, we have a situation wherein the offset feature has been active in the past, but should now be deactivated intentionally. Thus, HR1_Offset is set to 0 (box 71), and a final broken vertical line, as well as an additional label indicating zero offset, will be drawn (step 72).

Figure 9:
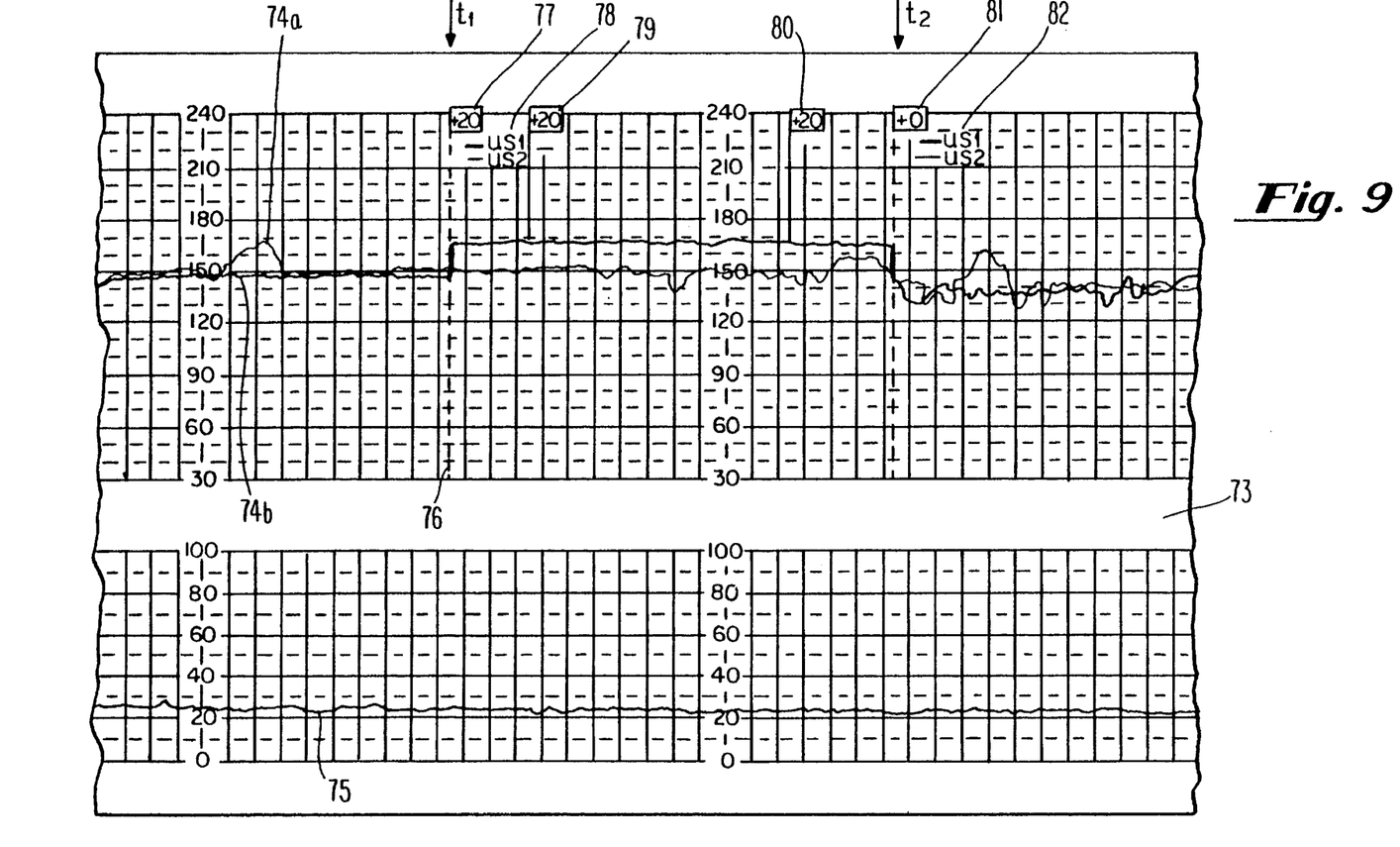
FIG. 9 depicts the recorder paper with heart rate traces recorded according to the present invention.

FIG. 9 depicts a typical recorder print-out obtained with the present invention on recorder paper 73. The two fetal heart rate traces (originating from twins, or even from fetuses of different mothers) are labelled as 74a and 74b. The toco trace is labelled as 75, but it is not of further importance herein.

At time $t_1$, the user has noted the overlapping of the two heart rate traces, and has activated, in the manner described above, the offset shift of the first heart rate. A vertical line 76 has been drawn, in addition to a label 77 which indicates, by means of its inverted numerics "+20", the amount of offset shift. Further, the trace patterns of the two heart rate traces are annotated as indicated by label 78 (in the shown example, the two heart rates are recorded by means of lines with different thickness). The annotations "US1" and "US2" show that the respective trace signals have been obtained by means of an ultrasound transducer.

Starting at $t=t_1$, heart rate trace 74b is recorded with an offset of +20 bpm. It is evident that no further overlapping of the traces occurs, such that even the variability may be reliably assessed. In practice, readability will further be increased by the fact that the grids have been preprinted in a different color than the trace recordings.

In order to indicate that the first heart rate has been recorded with an offset, a "flag" 79 is printed 15 mm after the onset of the offset shift. This flag consists basically of a label including the numerical value of the offset, and a bar which connects the label with the shifted heart rate. This "flag" is then repeated every 50 mm, see for example flag 80. At $t=t_2$, the user has switched OFF the offset feature. Another broken vertical bar is printed, together with a label 81 indicating an offset of 0. The annotation regarding the trace patterns is repeated, see reference Number 82. After deactivation of the offset shift, heart rate traces 74a and 74b overlap again.

Up to now, only embodiments with manual activation/deactivation of the offset shift have been discussed. However, under certain circumstances, it may be desirable to detect the necessity for the activation of the offset shift on an automatic basis. One suitable method for performing such automatic detection will now be explained with reference to the flow charts in FIGS. 10a–10c.

Figure 10A:
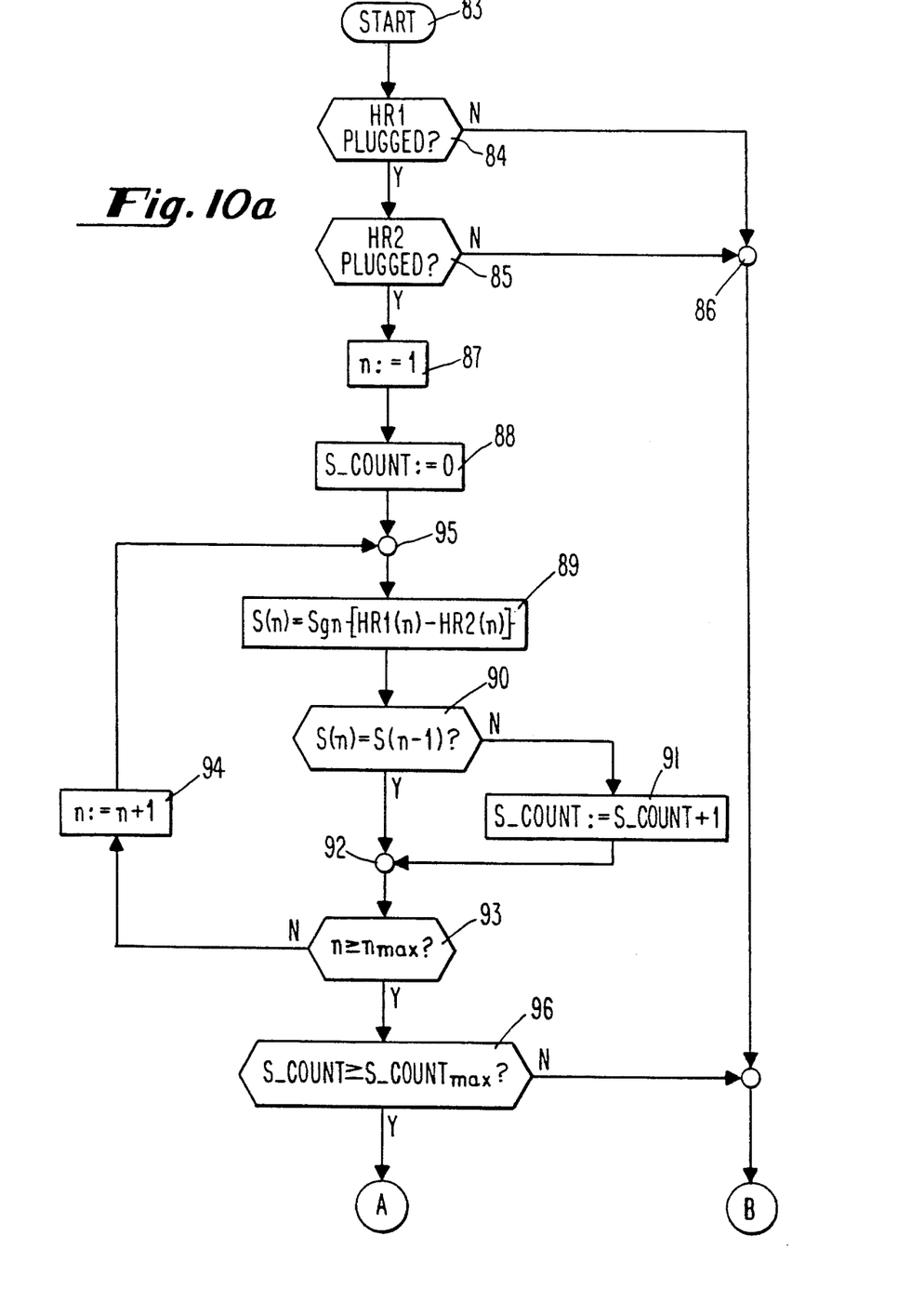
FIGS. 10a–10c are flow charts illustrating one possible implementation of automatic detection of the need to activate the offset feature.

After entry at "START" label 83, two tests are performed (steps 84 and 85) to ensure that both heart rate signals are present. If this is not the case, operation continues at node 86 which leads to label "B".

In case both heart rates are present, n is set to 1 (box 87), and a variable S_Count is set to 0 (box 88).

In step 89, the sign of the difference between the two heart rates, at a given point in time or at a given sequential number n, is determined. It is then tested (step 90) whether this sign is equal to the preceding one. If not, the variable S_Count is increased by 1 (box 91); otherwise, operation proceeds directly to node 92.

The test performed in step 93 relates to the maximum of n, namely $n_{max}$. Thus, steps 89–92 are performed over a predefined time or sequential interval which is determined by $n_{max}$. If n has not yet reached its maximum value, it is increased by 1 (step 94), and operation continues at node 95.

In case n has reached its maximum value, operation continues with test 96. At this point in time, the amount of variable S_Count represents the number of zero crossings over a predefined interval of heart rate samples.

Step 96 tests variable S_Count against a limit S_Count$_{max}$. In case this limit has been exceeded, operation continues at label "A" otherwise at label "B".

Now let us assume that the number of zero crossings exceeds the limit S_Count$_{max}$, which is a first indication that the two heart rate traces overlap considerably. If this is the case, operation continues at label "A" on the top of FIG. 10b.

Figure 10B:
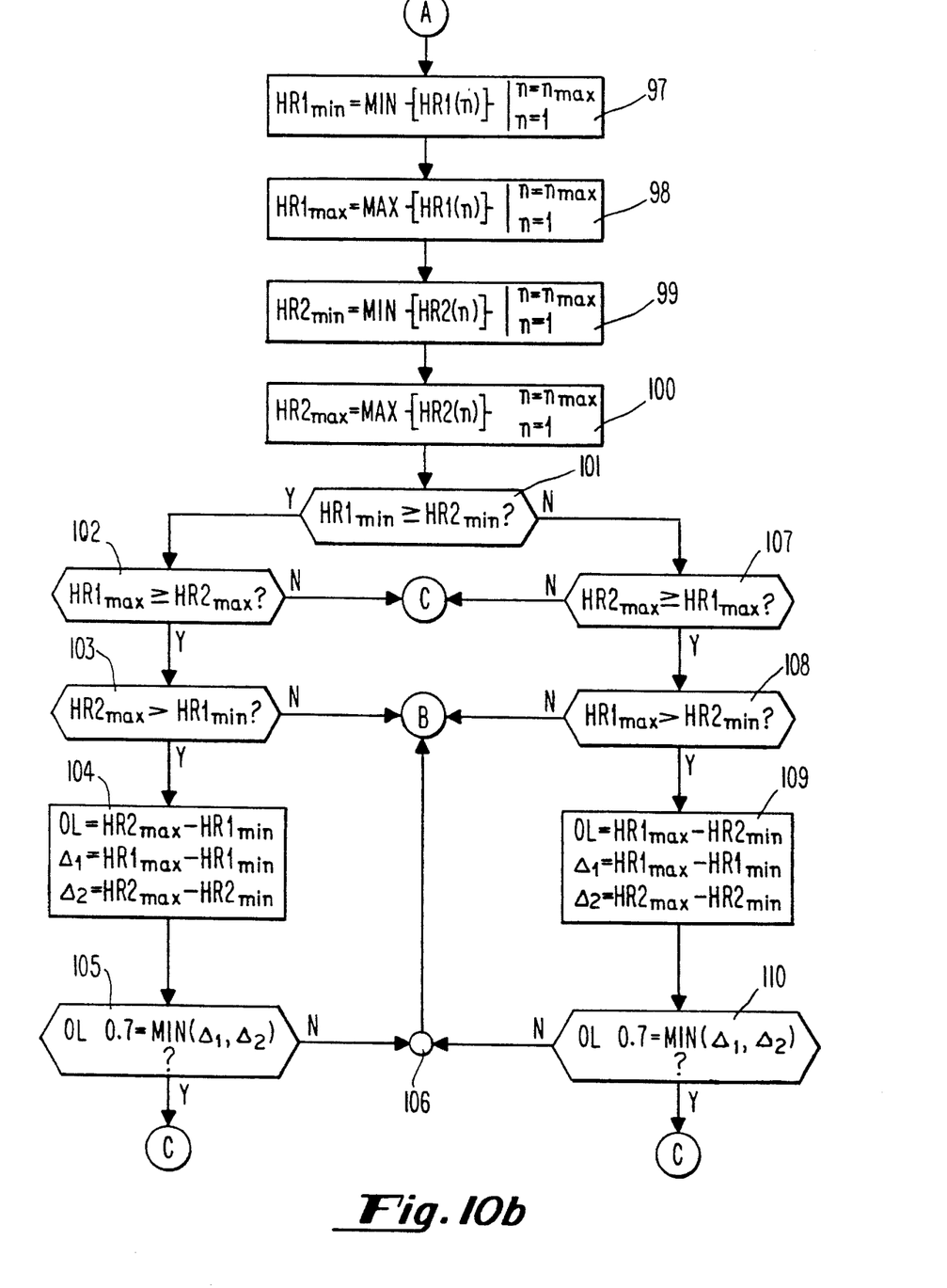

The steps performed in the flowchart of FIG. 10b test whether the ranges of the two heart rates overlap considerably. First, the minimum and maximum values of the two heart rates HR1 and HR2, in a given interval between n=1 and n=$n_{max}$, are determined, see steps 97–100. In step 101, the minimum values of the two heart rates are tested against each other. Let us assume now that the minimum of HR1 is greater than the minimum of HR2. In this case, the next step is test 102. This step tests the maximum values of the two heart rates against each other. In case the maximum value of HR1 is smaller than the maximum value of HR2, the range of HR1 lies completely in the range of HR2. In this case, operation proceeds to label "C".

If, on the contrary, the maximum value of HR1 is greater than the maximum value of HR2, a further test has to be made (step 103). If the maximum value of HR2 is smaller than the minimum value of HR1, the ranges of the two traces do not overlap at all, and operation continues at label "B". Otherwise, the calculations in box 104 are performed, wherein the variable OL indicates the overlap of the two ranges, and $\Delta_1$ and $\Delta_2$ are the respective ranges themselves. Step 105 performs a test for the significance of the overlap. In case the overlap area is greater than a certain amount of the smaller of the two ranges, the observed overlap is considered as significant, and operation proceeds to label "C". Otherwise, the overlap is not significant, and operation continues—via node 106—to label "B".

In the given example, the overlap must be greater than 0.7 times the smaller of the two trace ranges. However, it will be appreciated that this constant can be adapted to any desired and adequate value.

Steps 107–110 relate to the second case wherein the minimum of HR1 is smaller than the minimum of HR2.

Figure 10C:
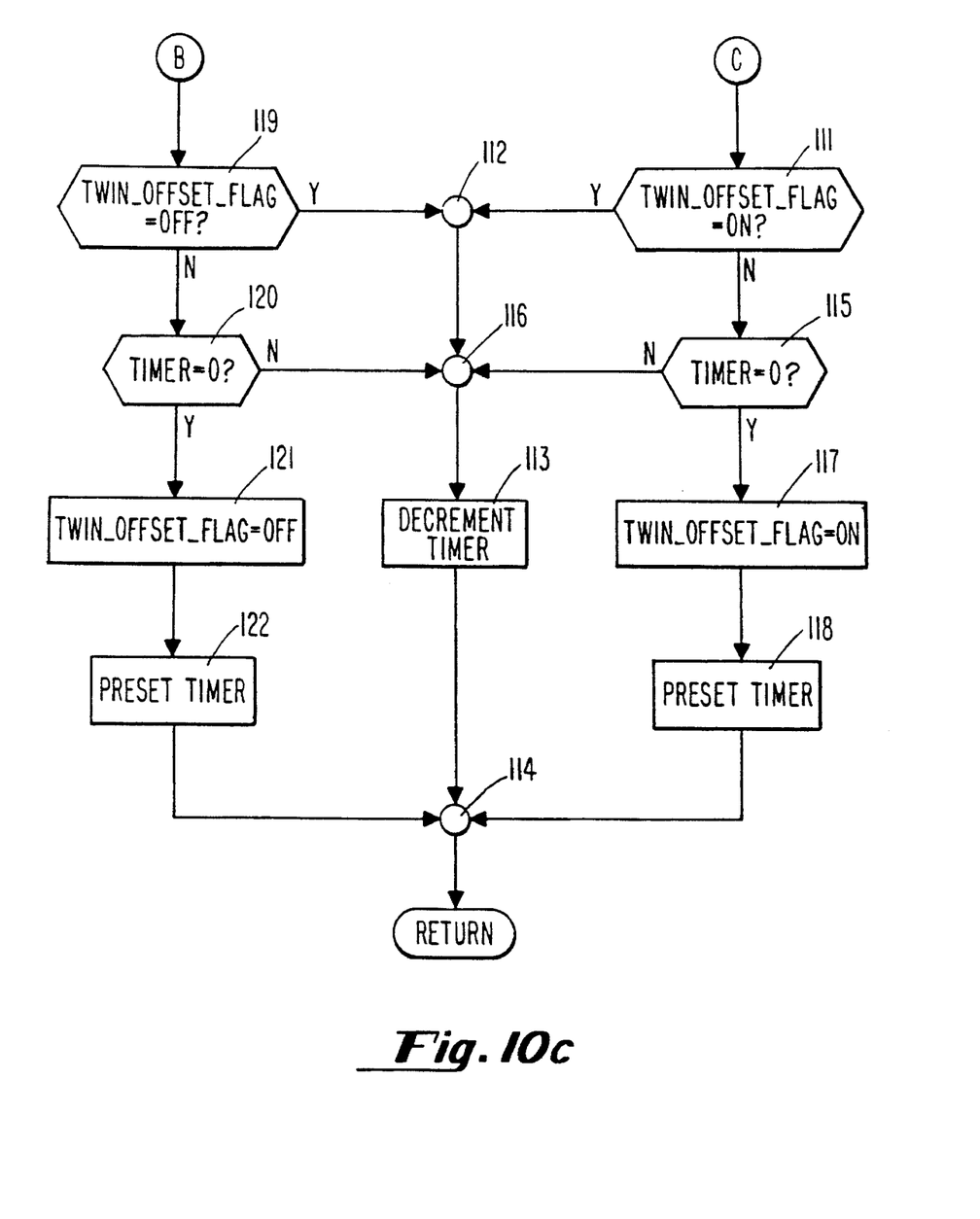

Let us continue now with the flowchart in FIG. 10c. The entry to this flowchart is labelled "C" if there is a strong indication that the two heart rate traces overlap, namely a significant number of zero crossings, and a significant overlap of the two heart rate ranges. Similarly, the flow chart is entered at label "B" if there is no indication for a necessity to activate the offset shift.

Let us first consider the path starting at label "C". In this case, it is first tested (reference No. 111) whether the offset shift is already active. If this is the case, operation continues at node 112. A timer is decremented (step 113), and operation stops (via node 114).

If the test in step 111 reveals a negative result—i.e., there is an indication that the offset shift should be turned ON, but it is not yet active—, a timer is tested in step 115. This timer is provided to avoid too frequent switching between the ON and OFF states of the offset shift, or, in other words, to implement a hysteresis. In case the timer has not yet counted to 0, the current state is kept, via node 116. Otherwise, Twin_Offset_Flag is set to ON indicating a necessity to switch to a heart rate shift (step 117). Further, the timer is restarted (box 118).

Similar operations are performed in steps 119-122 for the case of a negative offset indication.

It will be appreciated that Twin_Offset_Flag may be used in various embodiments. For example, it could turn on a lamp or an alarm, to give the user an indication of the necessity to switch. Activation or deactivation of the offset shift is then performed by the user manually. This is the "semi-automatic" mode of operation.

Alternatively, the status of Twin_Offset_Flag could also be used to switch the offset shift ON and OFF on an automatic basis (fully automatic mode of operation). In this embodiment, the state of Twin_Offset_Flag can be directly used in the diagram of FIG. 8, for example in step 54.

What is claimed is:

1. A method for recording at least two physiologic signals originating from different sources, comprising the steps of:
   sensing at least two physiologic signals;
   recording a trace of each said physiologic signal so sensed on a medium having a grid with predefined scaling;
   at least one of said physiologic signals being recorded on the grid relative to said predefined scaling;
   at least one of said physiologic signals being recorded on the grid with an offset relative to said predefined scaling;
   switching between a first mode wherein said physiologic signals are recorded relative to said predefined scaling, and a second mode wherein at least one of said physiological signals is recorded with an offset relative to the predefined scaling; and
   providing a detector for automatic detection of at least two physiologic signals being recorded on said grid and within the same range of the predefined scaling on said grid.

2. The method according to claim 1, wherein said physiologic signals are fetal heart rates from at least two fetuses, and said fetal heart rates are monitored using a fetal monitor.

3. The method according to claim 1, wherein said recording on said medium is provided by a recorder.

4. The method according to claim 3, wherein said recorder is a thermal printer.

5. The method according to claim 3, further comprising the step of:
   loading said recorder with paper having said grid with said predefined scaling preprinted thereon.

6. The method according to claim 5, wherein said grid is preprinted in a color different from the color of said traces recorded.

7. The method according to claim 3, further comprising the steps of:
   loading said recorder with paper; and
   printing said grid having said predefined scaling on said paper and further recording said physiologic signals on said grid with said recorder.

8. The method according to claim 3, wherein said step of recording further comprises the step of:
   printing a first identification relative to at least the physiologic signal being recorded with said offset relative to the predefined scaling.

9. The method according to claim 8, wherein said step of printing further comprises the step of:
   printing said physiologic signals with different trace patterns.

10. The method according to claim 8, wherein said step of printing further comprises the step of:
    printing said physiologic signals in different colors.

11. The method according to claim 8, wherein said step of printing, further comprises the step of:
    printing at least one label assigned with said physiologic signal being recorded with said offset relative to the predefined scaling.

12. The method according to claim 11, wherein said label includes the numeric value of said offset.

13. The method according to claim 11, further comprising the step of:
    printing a connection line connecting said label and said physiologic signal so recorded with said offset relative to the predefined scaling.

14. The method according to claim 11, further comprising the step of:
    repeating said printing step in predefined time intervals.

15. The method according to claim 1, wherein user-actuatable switches are provided for switching between said first mode and said second mode.

16. The method according to claim 15, wherein said user-actuatable switches include keys.

17. The method according to claim 15, wherein said user-actuatable switches include a bar code reader.

18. The method according to claim 1, further comprising the step of:
    generating a signal in response to said automatic detection by said detector.

19. The method according to claim 1, further comprising the steps of:
    automatically switching to said second mode when said two physiologic signals in the same range are so detected, and
    automatically switching to said first mode when said two physiologic signals in the same range are no longer detected by said detector.

20. The method according to claim 1, further comprising the step of:
    counting the zero crossings of said two physiologic signals over a predefined time period.

21. The method according to claim 1, further comprising the steps of:
    comparing a minimum and a maximum value from each of at least two said physiologic signals; and
    determining, based on said minimum and maximum values, whether said physiologic signals overlap by more than a predetermined amount.

22. The method according to claim 1, further comprising the step of:
    automatically conforming said offset to the degree of coincidence between said two physiologic signals.

23. The method according to claim 1, wherein said step of recording further comprises the step of:
    printing a second identification upon switching between said first mode and said second mode, and upon switching between said second mode and said first mode.

24. The method according to claim 23, wherein said step of printing, further comprises the step of:
    printing a line crossing the traces of said two physiologic signals.

25. The method according to claim 23, wherein said step of printing further comprises the step of:

printing at least one label assigned with said physiologic signal being recorded with said offset relative to the predefined scaling.

26. The method according to claim 25, wherein said label further comprising the numerical value of said offset.

27. The method according to claim 23, wherein said step of recording further comprises the step of:

printing the actual time.

28. The method according to claim 1, wherein said medium is a display.

29. The method according to claim 2, wherein ultrasound waves are transmitted in the direction of a fetal heart of each of said two fetuses, further comprising the step of:

processing the ultrasound waves reflected by each fetal heart and determining a Doppler shift therefrom;

generating a Doppler trace having peaks based on the Doppler shifts so determined; and each said trace being indicative of each fetal heart rate, each fetal heart rate being determined by the inverse of an interval between two subsequent peaks in the Doppler trace.

30. A medical monitor for recording at least two physiologic signals originating from different sources comprising:

recording means for recording at least one of said physiologic signals on a grid having a predefined scaling and further for recording at least one of said physiologic signals with an offset relative to said predefined scaling;

switching means coupled to the recording means for switching between a first mode wherein said physiologic signals are recorded on said grid relative to said predefined scaling, and a second mode wherein at least one of said physiologic signals is recorded with said offset relative to the predefined scaling; and automatic detection means coupled to said switching means for determining whether said two physiologic signals are in the same range relative to said predefined scaling.

31. The medical monitor according to claim 30, wherein said physiologic signals are fetal heart rates from two fetuses, and said medical monitor is a fetal monitor.

32. The medical monitor according to claim 30, further comprising:

user-actuatable switching means coupled to said switching means for causing said switching means to switch between said first and second modes.

33. The medical monitor according to claim 32, wherein said user-actuatable switching means comprises keys.

34. The medical monitor according to claim 32, wherein said user-actuatable switching means comprises a bar code reader.

35. The medical monitor according to claim 30, further comprising:

signal generation means coupled to said automatic detection means for providing a signal if said two physiologic signals are determined to be in the same range by said automatic detection means.

36. The medical monitor according to claim 30, wherein said switching means automatically switches between said first and second modes in response to the determination of the automatic detection means.

* * * * *